United States Patent
Capetanopoulos (10) Patent No.: US 7,030,990 B2
(45) Date of Patent: Apr. 18, 2006

(54) CONTROLLED INTERFERENCE SPECTROMETER

(75) Inventor: Constantine Dean Capetanopoulos, New York, NY (US)

(73) Assignee: Bah Holdings, LLC, Massapequa, NY (US)

( * ) Notice: Subject to any disclaimer, the term of this patent is extended or adjusted under 35 U.S.C. 154(b) by 197 days.

(21) Appl. No.: 10/182,844

(22) PCT Filed: Feb. 20, 2001

(86) PCT No.: PCT/GB01/00711

§ 371 (c)(1),
(2), (4) Date: Oct. 9, 2002

(87) PCT Pub. No.: WO01/65219

PCT Pub. Date: Sep. 7, 2001

(65) Prior Publication Data

US 2003/0090670 A1    May 15, 2003

(30) Foreign Application Priority Data

Mar. 2, 2000 (GB) .................................. 0005069

(51) Int. Cl.
*G01B 9/02* (2006.01)
(52) U.S. Cl. ...................................................... 356/454
(58) Field of Classification Search ................ 356/454, 356/519, 419, 416

See application file for complete search history.

(56) References Cited

U.S. PATENT DOCUMENTS

| | | | |
|---|---|---|---|
| 4,320,973 A | 3/1982 | Fortunato et al. | |
| 4,602,342 A | 7/1986 | Gottlieb et al. | |
| 4,652,756 A | 3/1987 | Ryan et al. | |
| 4,653,869 A | 3/1987 | Gottlieb et al. | |
| 4,663,961 A | 5/1987 | Nelson et al. | |
| 4,732,480 A | 3/1988 | Fortunato et al. | |
| 4,771,629 A * | 9/1988 | Carlson et al. | 73/23.35 |

FOREIGN PATENT DOCUMENTS

| | | |
|---|---|---|
| EP | 0 349 839 | 6/1989 |
| EP | 0 359 213 | 9/1989 |
| EP | 396319 A1 * | 11/1990 |

* cited by examiner

*Primary Examiner*—Andrew H. Lee
(74) *Attorney, Agent, or Firm*—Barnes & Thornburg LLP; James B. Conte (57) ABSTRACT

A spectrometer for determining the concentration of a substance within a sample comprises a. a radiation source (11) for supplying radiation to the sample to be measured; b. a filter (15) for filtering radiation transmitted by the sample, the filter having a number of pass bands at wavelengths corresponding to absorption peaks in the absorption spectrum of the sample to be detected, the filter being responsive to an applied signal to modulate the wavelengths of the pass bands; and, c. a detector (16) for detecting the filtered radiation, the detector being responsive to the applied signal to determine the relative intensities of the maxima and minima in the absorption spectra of the substance, characterized in that the radiation source is selectively activated in response to the applied signal.

23 Claims, 9 Drawing Sheets

{C=Optical axis}

CONTROLLED INTERFERENCE SPECTROMETER

The present invention relates to an improved controlled interference polarization spectrometer (CIPS) for determining the concentration of a substance within a sample, and in particular for optically detecting gases.

Optical methods for the detection of gases are based on the measurement of the absorption of incident radiation by the gas molecules. For any given wavelength of incident radiation, the quantity that is absorbed is a function of the "cross section" $\sigma(\lambda)$ ($cm^2$) of any particular molecule in the gas (i.e. the amount of absorption depends on the wavelength). If the dependence of the cross section on the wavelength is very pronounced, then the gas molecules will absorb radiation over a very narrow waveband. Accordingly, the spectral displacement between the maximum and minimum intensities of the transmitted radiation is very small. By measuring the difference between the maximum and minimum intensities of the transmitted radiation, it is possible to calculate the concentration of the gas.

Figure 1A:
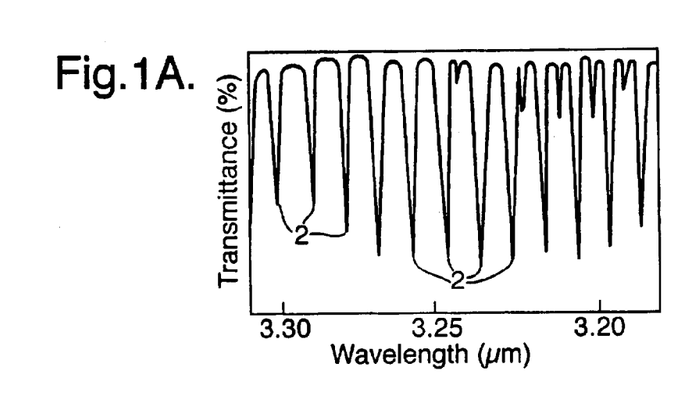
FIG. 1A is a graph of the absorption spectrum of methane.

In the case of a CIPS, this uses the quasi periodical structure of the electronic absorption spectrum of the gas molecules, which is due to their vibrational-rotational properties. An example of such an absorption spectrum is provided in FIG. 1A which shows the absorption spectrum of methane, in the vicinity of 3.25 micrometers. This vibration-rotation spectrum consists of a number of very narrow (approximately 1 nm wide) quasi periodic absorption bands 2 that are detected by the CIPS.

This quasi periodic structure depends on the vibration and rotation of the gas molecules, and accordingly, this form of spectra is highly resolved such that the quasi periodic structure of the gas molecules absorption is well defined.

In order to detect the quasi periodic structure, the CIPS filters radiation transmitted by the sample gas using a comb filter which is generated by a controlled Interference Polarization Filter (cIPF). The cIPF is formed from a modified Interference Polarization Filter (IPF) which uses the phenomenon of birefringence in certain crystals to obtain a transmission spectrum which is characterized by a quasi periodic sequence of spectral pass bands.

In order to be able to use the IPF in the detection of gases, the IPF must provide a transmission spectrum that closely matches the quasi periodical absorption spectra of the gas to be detected (i.e. the bandwidth between adjacent peaks in the absorption spectrum of the gas to be detected must correspond to the bandwidth between adjacent transmission peaks in the "IPF" transmission spectrum). Furthermore the IPF must be able to shift this spectrum in time, so that one can detect the intensity of the radiation transmitted at both of the absorption and non absorption bands of the absorption spectrum of the target gas.

In order to achieve this, the IPFs are modulated by changing any of the following characteristics:

(1) change the width of the natural birefringent section;
(2) change the type of birefringent material used; or,
(3) introduce an additional birefringent section.

The spectral scanning of the radiation passing through an IPF can therefore be accomplished in a number of ways. For example, by mechanically rotating the output polarizer by 90°, with respect to the optical axis of the birefringent crystal. Alternatively nematic liquid crystals can be used together with an IPF to achieve tuneability. However, the most versatile method is the use of a Photoelastic Modulator of Polarization (PMP), which will be explained in more detail below.

The bandwidth of the generated pass bands in the transmission spectrum will depend on the type of IPF used. Typically, narrower bandwidth pass bands are defined by more complicated multipass filters, such as a SOLC or Lyot filters. However, these filters are more complicated than simpler single pass filters, such as a Woods filter, and therefore more cost more to produce and maintain.

However, even using the complicated multipass filters, each of the transmission peaks in the comb filter defined by the cIPF has a finite bandwidth. Accordingly, the resolution of gas detectors using this system is still limited. Furthermore, the use of the more complex cIPFs is prohibitively expensive and results in overly complex apparatus which is prone to failure.

In accordance with the present invention, we provide a controlled interference polarization spectrometer for determining the concentration of a substance within a sample, the spectrometer comprising:

a radiation source for supplying radiation to the sample to be measured;

a filter for filtering radiation transmitted by the sample, the filter having a number of pass bands at wavelengths corresponding to absorption peaks in the absorption spectrum of the sample to be detected, the filter being responsive to an applied signal to modulate the wavelengths of the pass bands; and, a detector for detecting the filtered radiation, the detector being responsive to the applied signal to determine the width of the absorption peaks, characterized in that the radiation source is selectively activated in response to the applied signal.

Accordingly, the present invention provides a controlled interference polarization spectrometer with an improved spectral resolution. This is achieved by selectively activating the radiation source in response to the applied signal so that radiation is only emitted from the source when a measurement is to be made by the detector. This effectively reduces the bandwidth of each transmission peak in the transmission spectrum of the filter, thereby improving the resolution of the spectrometer.

The spectrometer usually also includes a processor coupled to the detected for processing signals output therefrom. However, the signals may alternatively be stored for subsequent processing, or simply be displayed.

A further problem which is encountered with spectrometers of this form is ensuring that the bandwidth between adjacent transmission peaks in the IPF transmission spectrum correspond to the quasi periodic absorption spectra of the gas to be detected. Typically, in the prior art, this has been achieved by configuring the filter used to ensure that the correct transmission spectrum is obtained. As set out above, this is generally achieved by ensuring that the birefringent element of the IPF has the correct birefringence and this is achieved either by changing the width of the birefringent element, changing material used or adding an additional birefringence.

Even so, such birefringent crystals are typically temperature sensitive and it is therefore also necessary to control the temperature of the crystal within very strict parameters.

Figure 1B:
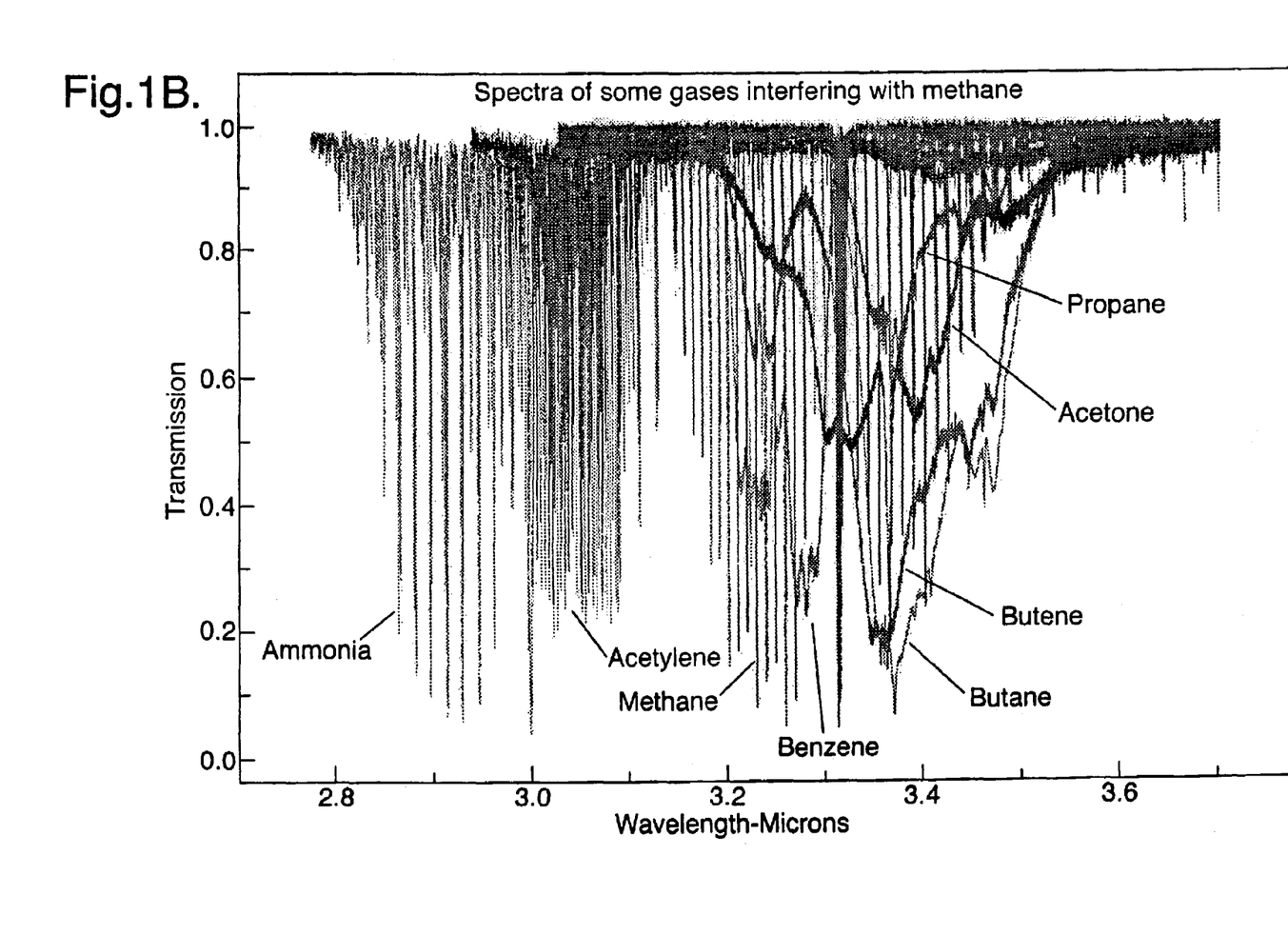
FIG. 1B is a graph of the absorption spectrum of methane and a number of other gases.

Once this has been achieved, it is necessary to ensure that the transmission spectrum corresponds to that of the gas to be detected. This causes an additional problem in prior art devices as a number of other gases have absorption spectra that not only fall in the range of the absorption spectrum of the target gas, but that also have spectra characterized by quasi perodic absorption lines similar to these exhibited by the target gas. An example of this situation in which the target gas is methane is shown in FIG. 1B. In this case, other gases such as Butane, Acetylene and the like have similar absorption properties.

In a standard CIPS system the detectors synchronization circuits are designed to distinguish and lock on to the maxima and minima of the absorption of the target gas.

If an interfering gas has a quasi periodic absorption structure within the desired band, the task of synchronizing the detector circuits to desired maxima and minima becomes more difficult.

In accordance with a second aspect of the present invention, a spectrometer for detecting the concentration of a substance within a sample, the spectrometer comprising:

a. a reference cell containing a quantity of the substance;
b. a sample cell for containing the sample in use;
c. a radiation source for supplying radiation to the reference cell and the sample cell;
d. first and second filters for filtering radiation transmitted by the reference and sample cells respectively, each filter having a number of pass bands and being responsive to an applied signal to modulate the wavelengths of the pass bands;
e. first and second detectors for detecting the filtered radiation from the first and second filters respectively, the detectors being responsive to the applied signal to measure the intensity of the filtered radiation; and,
f. a processor responsive to the first detector for controlling the applied signal.

Accordingly, the present invention provides a technique for fine tuning the filters used in the spectrometer to ensure that the passbands of the filters correspond to the width between adjacent peaks in the spectrum of the substance to be detected. This is achieved by using a reference cell containing a quantity of the substance and transmitting radiation through the cell and a filter and then measuring the output from the filter. The filter is then fine tuned by adjusting the signal applied to modulate the wavelengths of the passbands of the filter until the passbands of the filter correspond to the peaks in the quasi periodic absorption spectra of the substance. At this point, as the same signal is also applied to the filter which filters radiation from the sample cell, then this filter will also have a transmission spectra with passbands corresponding to the adsorption spectra of the substance, thereby allowing its concentration to be determined. This therefore ensures the system is configured correctly.

A further advantage originating from the addition of a reference gas cell is that the radiation detected from the reference cell corresponds exactly to the known concentration of the target gas inside the reference cell. By comparing the amplitude of this signal with the amplitude of the signal obtained from the sample cell, one can determine an exact value of the concentration of the desired gas in the sample.

Typically, the first and second detectors operate to repeatedly sample the intensity of the filtered radiation at the predetermined time intervals. This allows repeated measurements to be used in determining the intensities of radiation by either detector.

The processor controls the applied signal such that the first detector detects wavelengths of radiation corresponding to maxima and minima in the transmission spectrum of the substance of adjacent sampling times. Alternatively, the processor could control the applied signal to detect whether the wavelengths of radiation correspond to the maxima and minima at alternative sampling times, such as every $3^{rd}$ or $4^{th}$ sampling time.

The signal usually includes a bias signal and an alternating signal. Accordingly, the set up is usually achieved by controlling the bias signal such that the pass bands of the filter correspond to either the maxima or minima of the spectra of the substance when no alternating signal is applied.

However, the system does set itself to ensure that the first detector detects wavelengths of radiation corresponding to the maxima and minima intensities of the passbands of the absorption spectra of the substance to be detected.

Typically, the second detector samples the radiation transmitted by the second filter at the same time as the first detector samples the radiation transmitted by the first filter, in accordance with the same applied signal. However, alternative configurations such as sampling at alternative times may be used if the spectrometer is configured accordingly.

The processor preferably responds to the second detector to determine the difference in intensity of the radiation transmitted between adjacent sample times to thereby calculate the concentration of the substance within the sample.

Preferably, the or each filter comprises a first polarizer for polarizing received radiation;

a birefringent element responsive to the applied signal, wherein the birefringent element modifies the polarization of the polarized radiation in accordance with the wavelength of the radiation and the applied signal; and, a second polarizer for polarizing the radiation transmitted by the birefringent element. However, alternative designs of filter, such as diffraction filters may be utilized.

In the case in which the above mentioned filter is used, the birefringent element usually comprises a first birefringent member and an optically isotropic member being responsive to a force supplied thereto to generate a birefringence. However, a single element which has a natural birefringence and in which can be induced and additional birefringence can be used.

Typically the birefringent element is common to both filters. However, alternatively a separate birefringent element could be used for each filter with the birefringent element being controlled in response to the same applied signal.

The second aspect of the present invention may also be utilized to detect the concentration of a number of different substances within the sample. In this case, the spectrometer would include a number of different reference cells, with each reference cell containing a quantity of the substance to be detected. Each reference cell would then have a corresponding filter and detector designed to detect radiation transmitted therethrough.

It will also be appreciated that the first and second aspects of the present invention can be combined such that the reference cells are used in a spectrometer in which the radiation source is modulated.

Preferably the radiation source comprises an LED, which may be an LED that operates in the visible or infra-red wavelengths. Infra-red LEDs are particularly advantageous as they are capable of being modulated at extremely high frequencies making them ideal for use in the present invention. However, any radiation source that can be modulated in accordance with an applied signal, such as a lamp, a laser, or the like, could be used.

Preferably the spectrometer further comprises a collimator positioned between the radiation source and the sample for collimating the radiation emitted by the radiation source. However, this is not required if the radiation emitted from the source is suitably collimated.

The spectrometer may also include a bandpass filter positioned between the sample and the filter. This reduces the amount of radiation which is incident and helps remove radiation having a wavelengths not in the region of interest (i.e. within the region of the rotational-vibrational spectrum of the gas to be detected).

Example of the present invention will now be described with reference to the accompanying drawings, in which:—

Figure 2:
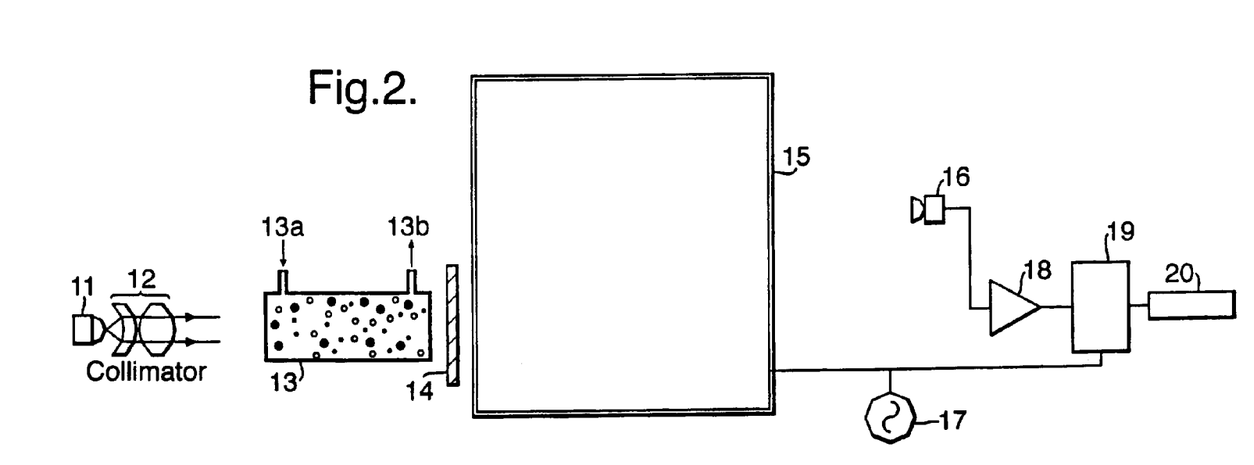
FIG. 2 is a schematic diagram of a prior art CIPS apparatus.

An example of a CIPS adapted to detect the quasi periodic structure of the gas molecules absorption spectrum is shown in FIG. 2.

This type of spectrometer can be operated either as an active device using an emitter, such as an incandescent lamp or as a passive device, using the sun as an emitter. The design shown in FIG. 2 is for an active CIPS system.

The CIPS includes a radiation source 11 such as an LED a LASER or the like positioned next to a collimator 12. The collimator operates to convert the incident radiation into a co-linear beam which then passes through a gas cell 13. The gas cells contains the gas to be detected and includes an input aperture 13a and an output aperture 13b. Radiation transmitted through the gas cell 13 is then filtered using a narrow band filter 14 which allows only wavelengths not in the vicinity of the desired absorption spectra to pass. Thus, for example, to detect methane then the bandpass filter would allow radiation in the 3.25 micrometer region to pass.

Following the filter 14 is a controlled interference polarization filter (cIPF) section 15. The cIPF 15 generates a transmission spectrum that consists of very narrow pass bands coinciding with the quasi periodic absorption spectrum of the target gas. The cIPF 15 is controlled to cause the transmission spectrum to be scanned back and forth within the selected working range. The operation of the cIPF 15 is controlled by an alternating voltage supply 17 which drives the cIPF and the detection system.

The detection system consists of a detector 16 coupled to an amplifier 18 which operates to amplify signals detected by the detector 16. The output of the amplifier 18 is coupled to a microprocessor 19 which is also coupled to the alternating voltage supply 17 so as so synchronize the processing of the detected signal with the operation of the cIPF 15.

Signals obtained from the microprocessor 19 are then output to a display 20 which displays an indication of the concentration of the detected gas.

Figure 3A:
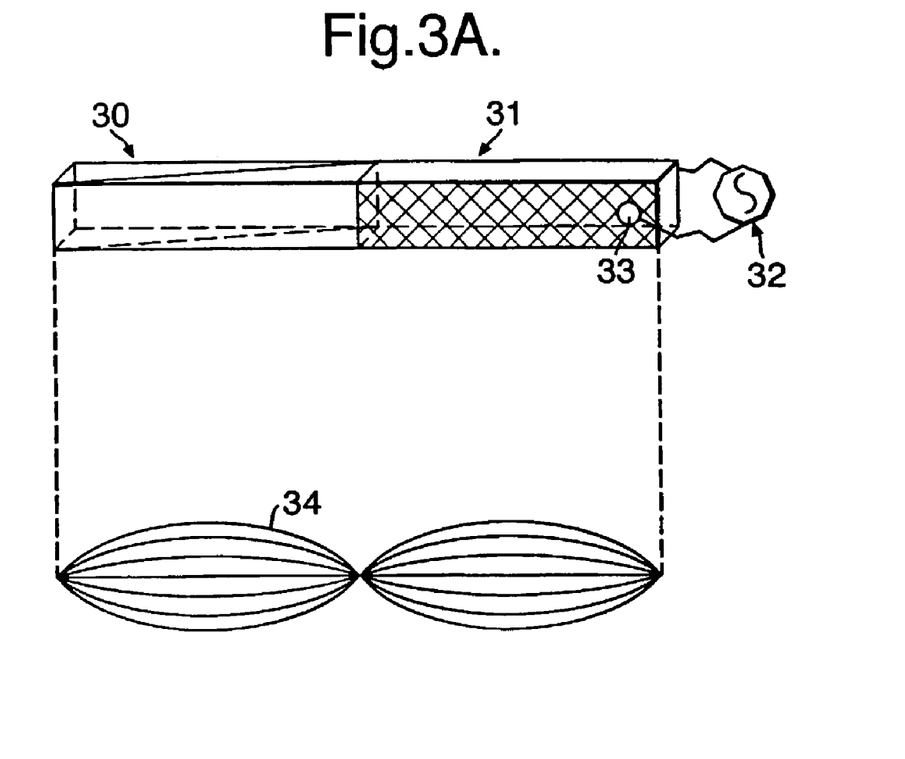
FIG. 3A shows an induced birefringent crystal for use in a Woods filter.

The cIPF 15 is formed from a modified Interference Polarization Filter (IPF) which, in the present example, is modified by the inclusion of a Photoelastic Modulator of Polarization (PMP), an example of which is shown in FIG. 3A.

The photoelastic modulator includes an isotropic material 30 such as fused quartz that is being mechanically stressed using a piezoelectric driver element 31 and an alternating voltage source 32. The stress is arranged to be applied periodically along one of the edges of the isotropic material 30 so that the isotropic material 30 generates an induced birefringence that is periodic with time.

The difference in the induced refractive indexes $(n_o - n_e)$ in the photo elastic modulator is proportional to the magnitude of the stress applied to the isotropic material 30 by the piezoelectric driver element 31. Accordingly, at any instant of time, the amplitude of the deformation determines the value of the induced birefringence, $\mu$. As a result the spectral location of the transmission maxima of the filter's pass bands is varied by changing the stress applied to the crystal.

In the cIPF, the lengths of the isotropic material 30 and the piezoelectric driver element 31 are selected so that the self resonant frequencies of longitudinal vibrations are equal. The frequency of vibration is then selected to generate a single full standing wave for the entire system, as indicated by the standing wave 34. This results in a standing half-wave being generated in the isotropic material 30. This establishes a maximum mechanical stress and hence a maximum value for $(n_o - n_e)$ in the middle of the isotropic material 30. The magnitude of the applied stress and therefore the magnitude of the birefringence $\mu$ therefore depends on the amplitude of the voltage driving the piezoelectric driver element 31.

In the cIPF, the maximum stress and therefore maximum birefringence for the isotropic material 30, is set to correspond to a phase retardation exactly equal to $\lambda/2$ (i.e. half wave retardation).

In the example shown, a section of fused quartz acts as the isotropic material 30 and a section of piezoelectric quartz acts as the piezoelectric driver element 31. The piezoelectric driver element 31 is driven by two electrodes only one of which is shown as electrode 33.

Figure 3B:
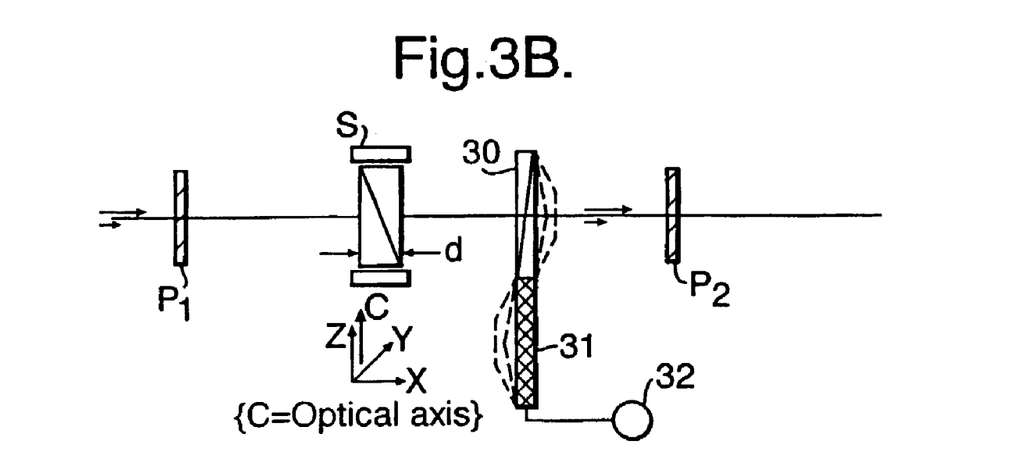
FIG. 3B is a schematic diagram of a Woods filter employing an induced birefringent crystal.

Operation of the PMP in a simple Woods IPF will now be described with reference to FIG. 3B. The Woods IPF includes input and output polarizers $P_1, P_2$ and an etalon formed from a birefringent crystal S. The birefringent crystal S can be either a traditional single axis crystal, such as quartz (having a birefringence index $\mu$ that varies from 0.01419 at $\lambda=185$ nm. to 0.0074 at $\lambda=3$ um.) or islandic spar (having a birefringence index $\mu$ that varies from 0.2028 at $\lambda=312$ nm. to 0.1606 at $\lambda=1.23$ um.) or a new type of crystal, such as paratelluride (having a birefringence index $\mu$ that varies from 0.185 at $\lambda=0.4$ um. to 0.14 at $\lambda=4.7$ um).

Figure 3C:
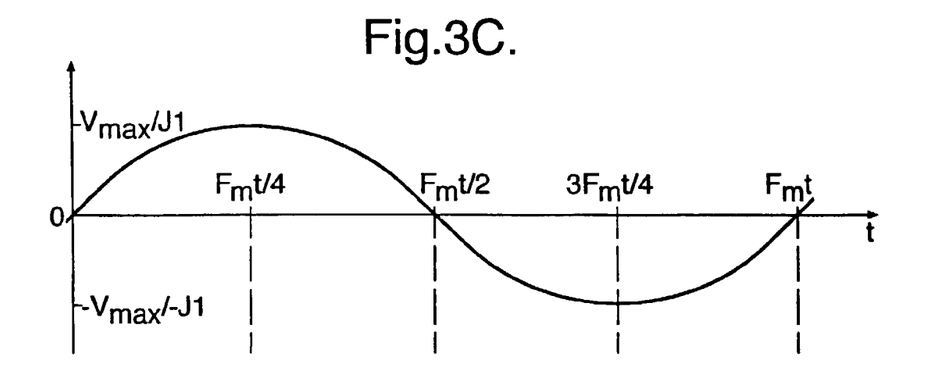
FIG. 3C shows the driver voltage applied to the apparatus of FIG. 3B against time.

Firstly, the PMP formed from the isotropic material 30, is arranged between the naturally birefringent crystal S and the polarizers $P_1, P_2$, as shown. In this case, a beam of radiation 35 incident on the polarizer $P_1$ as shown, passes through the middle of the isotropic material 30 as shown in FIG. 3C. In the undriven state the isotropic material 30 is not birefringent and therefore there are no changes in the passing beam and its spectral distribution.

The intensity of incident radiation 35 having a wavelength $\lambda_2$ coinciding with the $\lambda$max of the transmission of the IPF will be at the maximum and equal to Jo/2 (where Jo is the intensity of the radiation having a wavelength $\lambda_2$ incident on the input polarizer $P_1$). For these rays their polarization as they exit the IPF is linear and their polarization vector is aligned (parallel) to the polarization vector of the output polarizer $P_2$.

Meanwhile, radiation having a wavelength $\lambda_1$ corresponding to the $\lambda_{min}$ of the transmission of the IPF will have a minimum intensity equal to 0.

Figure 3D:
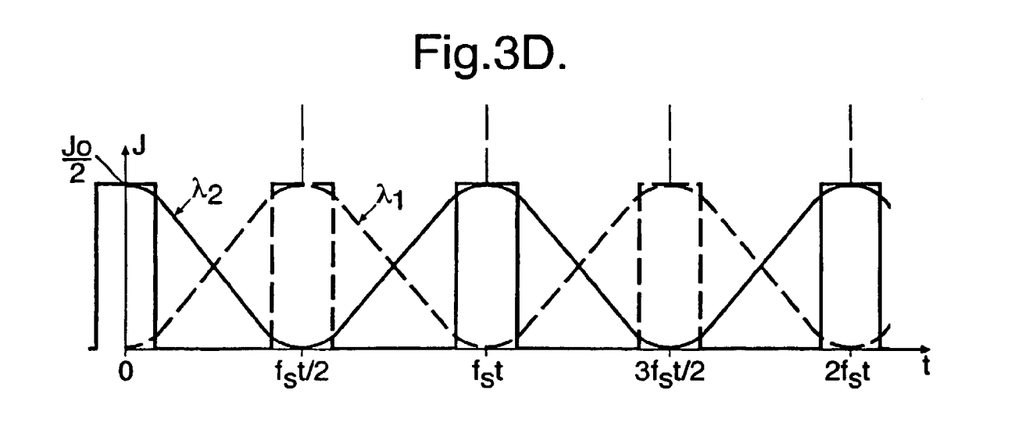
FIG. 3D shows the transmission intensity against time for the apparatus shown in FIG. 3B.

This is shown in FIG. 3D, which is a graph of the intensity of the transmitted radiation 35, for the wavelengths $\lambda_2$, $\lambda_1$ against time t. The voltage and hence stress applied to the isotropic material 30 is shown in FIG. 3C, using a similar time scale. Thus, at t=0, the applied voltage is zero, the intensity of the radiation 35 having a wavelength $\lambda_2$ is Jo/2, and the intensity of radiation having a wavelength $\lambda_1$ is 0.

As the induced birefringence is increased with the applied excitation the polarization vector for the radiation having a wavelength $\lambda_2$ exiting the isotropic material 30 becomes first elliptical, then circular, then elliptical again and finally, when the phase retardation becomes $\delta=\pi$, the exiting rays are again linearly polarized.

However, in this case the polarization vector is rotated by 90° with respect to the plane of polarization of the output polarizer $P_2$. Accordingly, the intensity of the radiation 35 exiting output polarizer $P_2$ and having a wavelength $\lambda_2$ reduces to a minimum.

As the birefringent crystal is driven sinusoidally with a frequency $F_m$, then the first minimum of transmission for the radiation 35 with the wavelength $\lambda_2$ will be at:

$$t=(F_m T/4)$$

Thus, at time intervals corresponding to $2n(F_m t/4)$ the output for the radiation 35 with the wavelength $\lambda_2$ will be a maximum whilst the radiation 35 having a wavelength $\lambda_1$ the intensity will be 0, as shown in FIG. 3D.

Maximum transmission for the wavelength $\lambda_2$ occurs when the phase retardation becomes $\delta=\pi$. Hence, for a time period corresponding to one full cycle of the driving frequency there will be two maxima and two minima outputs for the radiation having a wavelength $\lambda_2$. A similar situation exists for radiation having a wavelength $\lambda_1$ as shown.

Accordingly the frequency of change of the luminous flux (fs) is twice the selected modulation frequency of the crystal $fs=2F_m$.

Figure 3E:
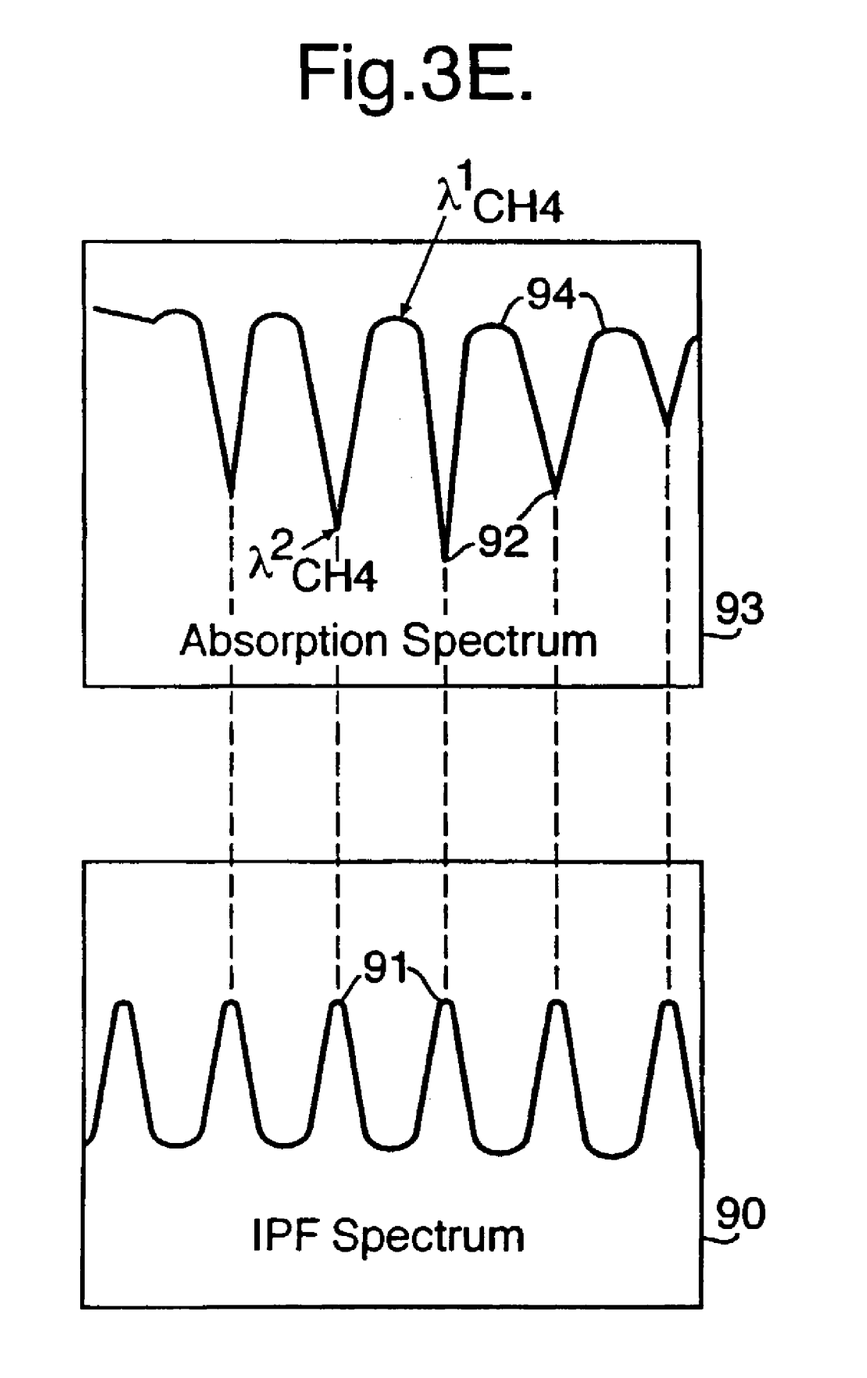
FIG. 3E is an example of the transmission spectrum of the apparatus of FIG. 3B, compared to the absorption spectrum of methane.

An example of the transmission spectrum of the cIPF is shown at 90 in FIG. 3E. The wavelength dependency of the birefringent effect means that the transmission spectrum of the cIPF includes a number of transmission peaks 91 (i.e. the cIPF acts as a comb filter). By choosing an appropriate birefringent crystal S, the transmission peaks 91 can be selected to correspond to absorption peaks 92 in the vibrational-rotational spectrum of the target gas which is shown at 93.

Accordingly, with the peaks 91,92 aligned as shown, the radiation transmitted by the cIPF will be the radiation having wavelengths which are absorbed by the target gas.

Furthermore, as a stress is applied to the isotropic material 30, the combined birefringence of the crystal S and the isotropic material 30 alters, causing the transmission spectrum of the cIPF to alter. Accordingly, the comb filter effectively scans from left-to-right and then back again.

When the transmission peaks 91 are aligned with troughs 94 in the vibrational-rotational spectrum 93, then the radiation transmitted by the cIPF represents wavelengths which are transmitted by the target gas. This allows the maximum and minimum transmission intensities in the absorption spectrum of the gas to be determined (i.e. the height of the peaks can be determined).

Thus, by choosing an appropriate amplitude driving signal, the cIPF can act as a modulator, scanning the vibrational-rotational spectrum of the sample gas from one maxima, to the next and back again. This makes the cIPF of FIG. 3B ideal for use in the apparatus of FIG. 2.

In this case, the microprocessor 19 is adapted to determine the intensity of radiation received at the detector 16 at the time when the peaks 91 of the cIPF transmission spectrum are aligned with the peaks 92, and then with the troughs 94, of the vibrational-rotational spectrum 93 of the target gas. By correlating this information with an indication of the relative transmission intensities of the cIPF, as shown in FIG. 3D, this allows the microprocessor to determine the relative intensities and the spectral displacement of the peaks 91 and troughs 94 in the vibrational-rotational spectrum 93. This in turn allows identification of the target gas to be achieved.

At the same time the transmission intensity of radiation having a wavelength $\lambda^1_{CH4}$ will be 0. Accordingly, the detector will detect a signal representative of the intensity of the radiation $\lambda^2_{CH4}$ which has been transmitted by the gas.

At time $T=F_s T/2$ the situation is reversed and the transmission peaks 91 of the transmission spectrum 90 of the CIPF 15 correspond to the troughs 94 in the absorption spectrum. Accordingly, only radiation having a wavelength $\lambda^1_{CH4}$ will be transmitted by the CIPF 15. The detector will therefore detect only radiation of this wavelength.

The detector transfers a signal representative of the intensity of received radiation to the processor 19. The processor 19 is coupled to the voltage generator 17 and uses a signal to monitor the output from the detector at time $T=NF_{MT}/4$. Accordingly, the processor 19 will obtain an indication of the intensity of the wavelength $\lambda^2_{CH4}$ at T=0, $F_{MT}/2$, $F_m/T$, . . . The processor 19 will also obtain an indication of the intensity of the wavelength $\lambda^1_{CH4}$ at times $T=F_{MT}/4$, $3F_{MT}/4$, . . .

This allows the processor 19 to determine the difference in intensities between the peaks 92 and the troughs 94, thereby allowing the concentration of the selected gas in the sample to be calculated.

Figure 4:
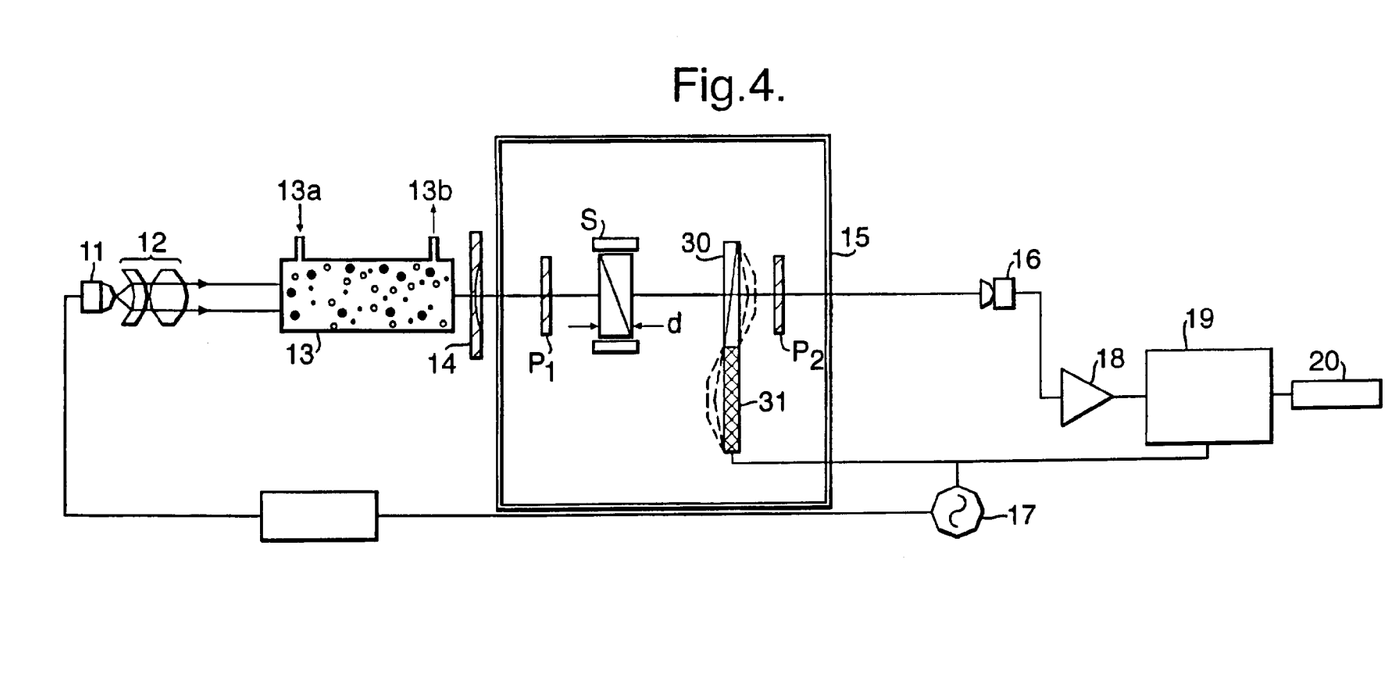
FIG. 4 is a schematic diagram of apparatus according to a first embodiment of the present invention.

An example of a CIPS in accordance with the present invention is shown in FIG. 4. This example is a modified version of the CIPS of FIG. 2 in which the voltage source 17 is also connected to the radiation source 11. Accordingly, the cIPF of FIG. 4 will have a transmission spectrum as described with respect to FIGS. 3B, 3C, 3D and 3E.

Figure 5:
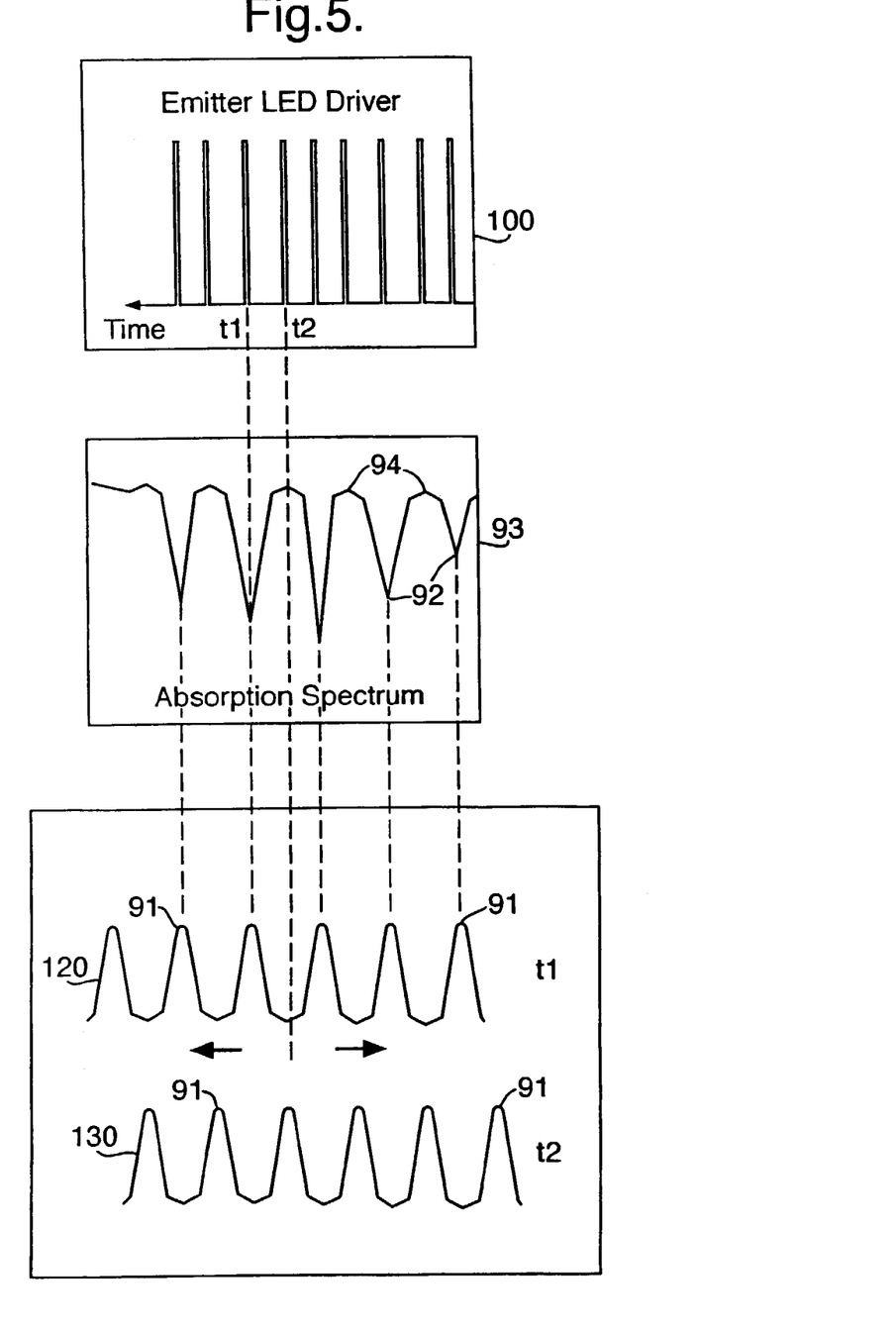
FIG. 5 is a schematic diagram representing the response of the radiation source and the cIPF of FIG. 4.

FIG. 5 includes a representation of the output of the radiation source 11 over time at 100. The vibrational-rotational absorption spectrum of methane is shown at 93, whilst the transmission spectrum of the cIPF 15 at time T1 and time T2 is shown at 120 and 130 respectively.

In the present example, the cIPF is configured such that at time T1 the peaks 91 of the cIPF transmission spectrum correspond to the peaks 92 of the methane absorption spectrum, whereas at time T2, the peaks 91 of the cIPF transmission spectrum correspond to the troughs 94 of the methane absorption spectrum.

As shown in FIG. 5, the radiation source is responsive to the applied signal so as to generate radiation only at times when the peaks of the cIPF transmission spectrum correspond to either the peaks or the troughs of the methane absorption spectrum. This corresponds to the detector generating radiation at times T1 and T2, and equivalent times in other cycles.

At all other times the radiation source 11 is inactive so that no radiation is generated. This results in the radiation source being activated for a very short time which is typically in the region of 10–50 microseconds.

The advantage of this improvement rests with the fact that since the spectral location of the gas absorption maxima are uniquely defined for the particular gas of interest, turning the emitter on and off at the precise timing interval ensures that no radiation is transmitted through the cIPF 15 when the cIPF transmission maxima do not correspond to a point of either maximum or minimum absorption by the target gas.

Accordingly, the detector is only able to make measurements at those precisely defined time intervals with no radiation being received at the other times. This eliminates the possibility of interference by unwanted absorptions from other interfering gases.

FIG. 1B shows the importance of enhancing the CIPS synchronization system by synchronizing the LED emitter operation with the maxima and minima of the absorption spectra of the target gas. The quasi periodic absorption spectrum of methane falls in the 3.2 to 3.5 micrometer region. However, as indicated in FIG. 1B a considerable number of other gases have a variety of absorption spectra in this region. Turning the emitter on and off at the precise instant of maxima and minima absorption of the target gas further enhances the selectivity of the system.

The detector 16 and microprocessor 19 then operate as in the example of FIG. 2 to determine the relative intensities and spectral displacement of the absorption peaks on the vibrational-rotational absorption spectra of the target gas, thereby allowing the gas to be identified.

This improvement enhances both the sensitivity and selectivity of the CIPS system.

Figure 6:
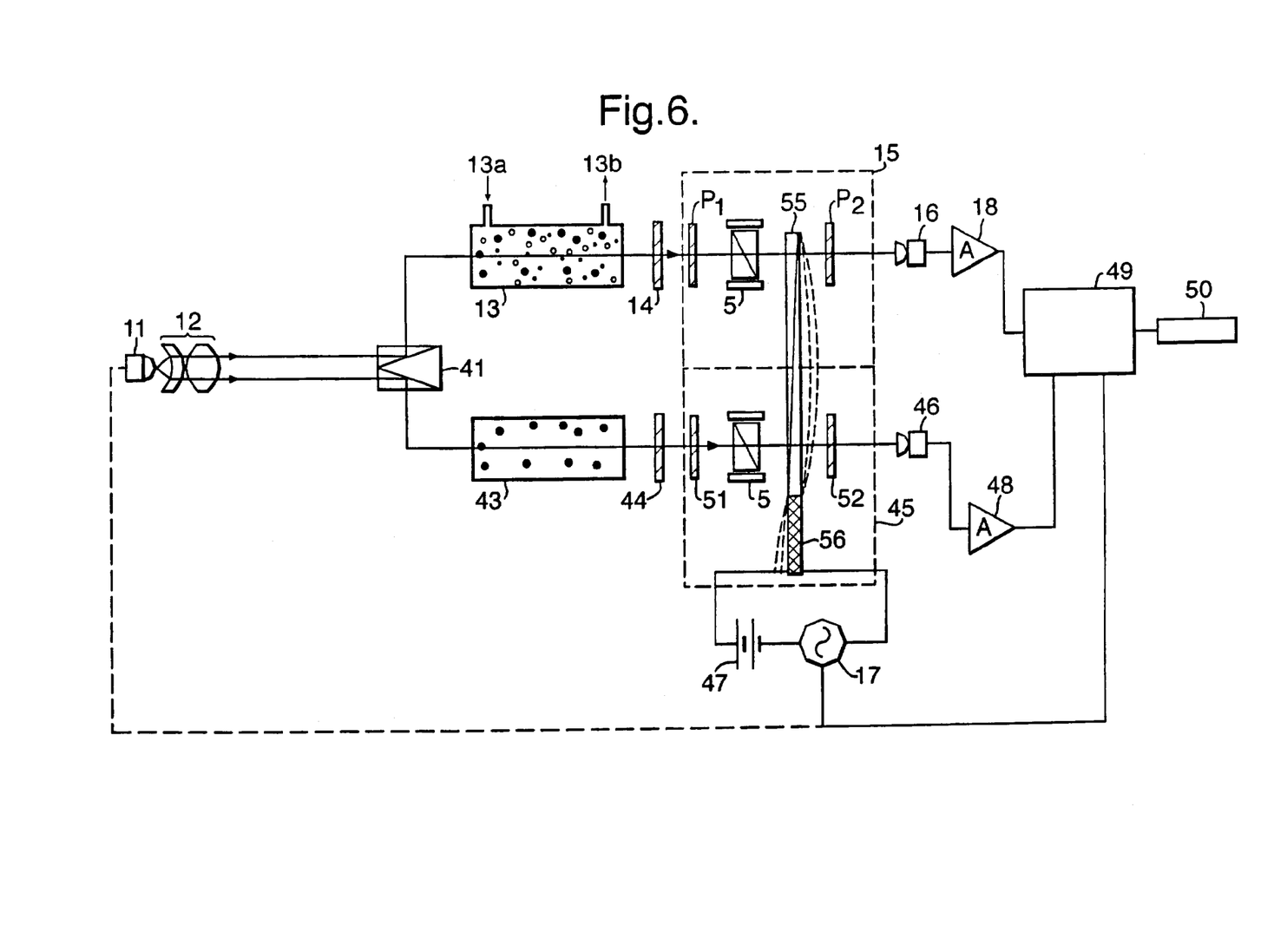
FIG. 6 is a schematic diagram of apparatus according to a second embodiment of the present invention; and, FIG. 7 is a schematic diagram of a second example of apparatus according to the second embodiment of the present invention.

FIG. 6 shows apparatus according to a second embodiment of the present invention. In this example, similar components to those used in FIG. 4 use similar reference numerals.

Accordingly, the apparatus comprises a radiation source 11 positioned next to a collimator 12. The radiation output from the collimator 12 is split by a beam splitter 41, such as a prism or the like, such that half the radiation passes through a sample gas cell 13 with the remaining radiation passing through a reference gas cell 42.

In use, the sample specimen which includes the target gas whose concentration is to be determined is placed in the gas cell 13. The reference gas cell 42 contains a pure sample of the target gas and this is used for reference purposes and for calibrating the operation of the spectrometer.

After the gas cell 13 and the reference gas cell 43 are provided respective narrow band pass filters 14,44 which only transmit wavelengths in the vicinity of the desired absorption spectra. Following each filter 14,44 is a respective controlled interference polarization filter (cIPF section), 15,45.

In this example, as in the example of FIG. 4, the cIPF 15 consists of first and second polarizers $P_1, P_2$ and a birefringent crystal S. Similarly the cIPF 45 includes a first polarizer 51, a second polarizer 52 and a birefringent crystal 53. In this example, the photoelastic modulator which is used in the cIPFs 15,45 is a single piece of isotropic material 55 coupled to a driver element 56. The isotropic material is positioned as shown such that radiation passing through either CIPF has to travel through a portion of the isotropic material 55.

As in the previous example, the driver element 56 is coupled to an alternating voltage supply 17 which operates to drive the driver element 56. In addition, a bias voltage supply 57 is also provided. The isotropic material 55 is positioned such that the induced birefringence that the radiation in each cIPF 15,45 is subject to is equal for all applied signals, as will be understood by a person skilled in the art.

Following the respective cIPFs 15,45 are respective detectors 16,46, respective amplifiers 18,48 and a microprocessor 49. The microprocessor 49 is also coupled to the alternating voltage supply 17 so as to synchronize the processing of the detected signal with the operation of the cIPFs 15,45. Signals obtained from the microprocessor 49 are then output to a display 50 which displays an indication of the concentration of the detected gas.

Operation of the present invention will now be described. In this example, the radiation which is output from the collimator 12 is split by the prism 41 such that half the radiation passes through the gas cell 13, the filter 14 and the cIPF 15 to the detector 16, whereas the other half of the radiation is transmitted through the filter 44 and the CIPF 45 to the detector 46. As mentioned above, the system is configured so that the amount of modulation provided by the isotropic material 55 is the same for each of the cIPFs 15,45. Accordingly, the signals obtained at the detectors 16 and 46 can be directly compared as will be described in more detail below.

As will be understood by a person skilled in the art, the portion of radiation which passes through the reference cell 43 will only be absorbed in wavelengths corresponding to the absorption spectrum of the target gas. Accordingly, the output from the cIPF 45 corresponds to a filtered version of the absorption spectrum.

If the cIPF 45 is configured correctly, then the maxima in the transmission spectra of the cIPF 45 will correspond to either the maxima or minima of the absorption spectrum of the target gas in the reference cell 43 when no alternating voltage is applied, for example as shown in FIG. 3E. Accordingly, subsequent readings by the detector 46 will yield results which should represent the maxima and minima in the absorption spectrum intensities which should be obtained for the target gas as the filter is scanned, as shown in FIG. 5.

If this is not the case, then the cIPF 45 is configured incorrectly such that the filter defined by the cIPF 45 will not be aligned with either the maxima or minima in the target absorption spectrum when no alternating voltage is supplied. Accordingly, the comb filter is not being scanned from peak to peak in the absorption spectrum of the target gas when the alternating voltage is applied.

To overcome this, the voltage generator 47 is used to apply a bias voltage to the driver element 56. This causes the driver element 56 to stress the optically isotropic material 55 causing a birefringence to be induced within the material. This effectively displaces the wavelengths of the points of maximum transmission for the cIPF. Accordingly, by controlling the bias voltage, the wavelengths between which the cIPF 15,45 scans can be controlled.

Thus, in the present invention, the bias applied by the bias voltage supply 47 can be gradually adjusted until the detector 46 detects the maximum and minimum intensities which should be obtained for the target gas when no alternating voltage is applied.

At this stage, it is known that the cIPF 15 is also configured correctly so that the comb filter of the cIPF 15 is scanning between maxima and minima of the absorption spectrum of the target gas As a result, the signals obtained from the detector 16 represent the maxima and minima in the absorption spectra of the target gas in the gas cell 13. From this, the concentration of the target gas within the sample can be calculated. This ensures that the detected intensities represent the maximum and minimum of the target gas and notg of some other contaminant gas in the sample cell.

It will be appreciated by a person skilled in the art that the microprocessor 49 can advantageously be coupled to the biasing device 47 and the detector 46 so as to automatically alter the bias voltage applied to the driver element 56. This allows the cIPF 45 to scan the absorption spectra of the reference gas, without the alternating voltage being supplied, until the transmission peaks in the spectrum of the cIPF 45 correspond to either the absorption peaks 92 or troughs 94 in the absorption spectra 93 of the reference gas. Once this has been completed, readings of the concentration of the target gas in the sample cell can be made in the normal way.

It will be realised that this embodiment of the present invention could also be implemented using separate photoelastic modulators in each cIPF 15,45. In this case, the single piece of isotropic material 55 would be replaced by respective pieces of isotropic material in each cIPF. However, the driver element of each respective isotropic material would be configured to apply identical stresses as the same voltage signals are applied to each driver element. This causes the generation of the same birefringence in each material so that operation is as described above.

It will also be realised that in this example of the present invention, the alternating voltage supply 17 could be connected to the radiation source 11 as shown by the dotted line such that the system also operates in accordance with the first aspect of the present invention.

The system described above can be extended, by including a number of additional different reference gas cells, such as one containing a known concentration of ammonia, another of acetylene etc. and by further splitting the emitter beam into three or more beams and using additional synchronization circuits to develop a multiple gas measuring CIPS system.

As the distances between the quasi periodic absorption lines are different for different gases, the bias voltage, which is superimposed with the alternating driving voltage, can be used to make a fine adjustment to the distance between maxima and minima of the target gas. Each reference gas cell can be associated with its own IPF which allows the cIPF associated with each reference cell to be adjusted to ensure the correct transmission spectrum is used for filtering radiation transmitted by the sample cell.

A slowly varying bias voltage is superimposed to the alternating driving voltage of the "unknown" IPF, causing the distance between the maxima and minima of the "unknown" IPF band pass to vary relatively slowly compared with the alternating voltage, this distance coinciding first with that of one target gas, then in sequence coinciding with that of the second gas and so on.

Figure 7:
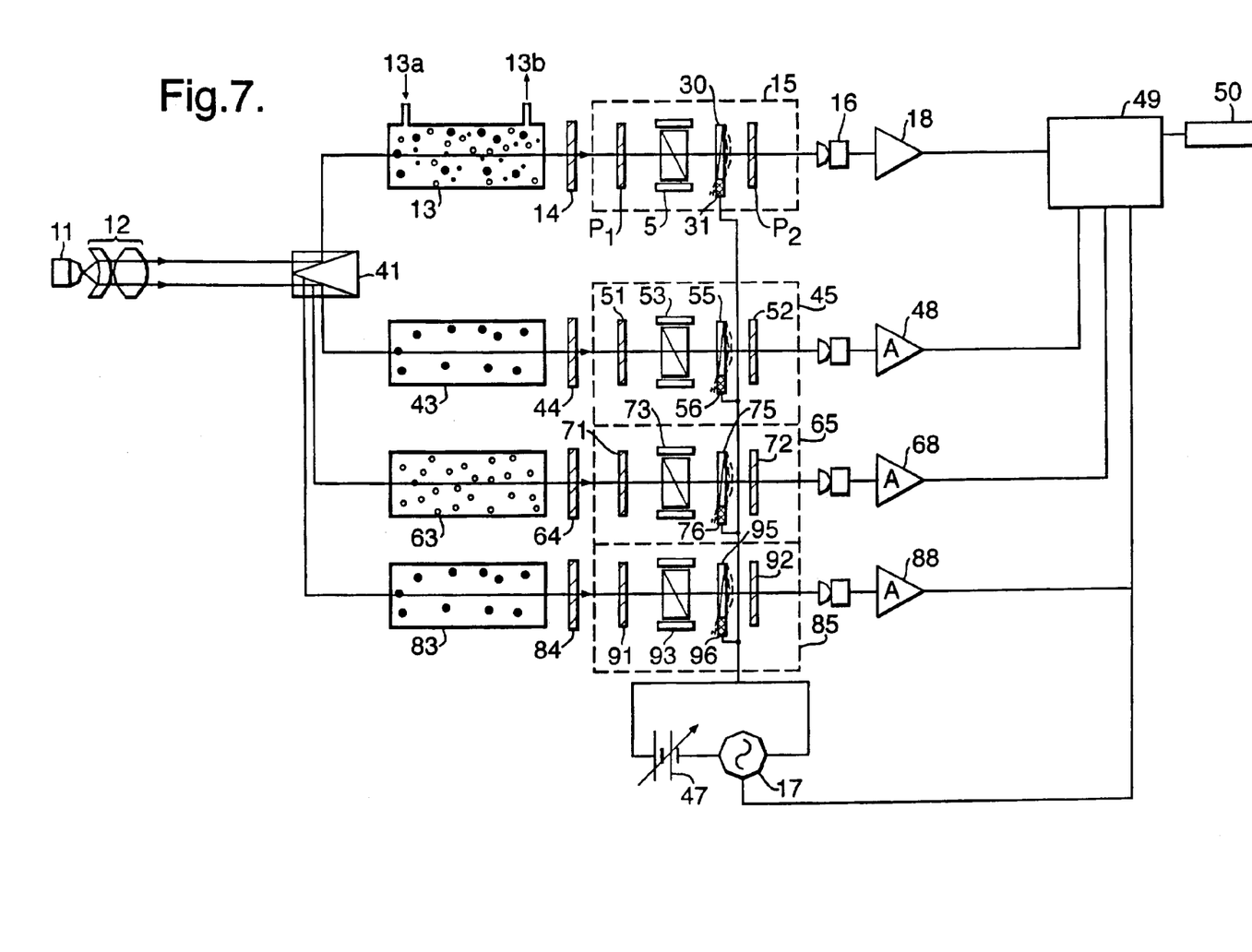

An example of such apparatus is shown in FIG. 7. Again, similar reference numerals to those used in previous diagrams are used as appropriate. In this example, three different reference cells 43,63,74 are provided for first, second and third respective target gases. A sample containing unknown proportions of each of the target gases is then placed in a sample cell 13.

Thus, in this example the beam splitter splits the collimated radiation into four equal portions. The first portion of the radiation passes through the gas cell 13, a filter 14 and a CIPF 15 to a detector 16. The detector 16 is connected via a amplifier 18 to a processor 49 which is in turn connected to a display 50. The second, third and fourth portions of the radiation pass through the reference cells 43,63,83, narrow band filters 44,64,84 and CIPFs 45,65,85 respectively. The radiation is then detected by respective detectors 46,66,86 and is fed via respective amplifiers 48,68,88 to the microprocessor 49.

In this example, each CIPF 15,45,65,85 includes a first and second polarizer 51,71,91,52,72,92 and respective birefringent crystals 53,73,93, as shown. Each CIPF also includes a respective photoelastic modulator consisting of a driver element 56,76,96 coupled to a respective piece of isotropic material 55,75,95 as shown. In this case, the isotropic materials 55,75,95 are arranged such that the birefringence induced for a given applied voltage is identical.

Operation of the system will then be similar to in the example of FIG. 6. Accordingly, the voltage applied to the driver elements 56,76,96 is controlled so as to ensure that at any one time the output obtained from one of the CIPFs 45,65,85 when no alternating voltage is applied corresponds to either the maxima or minima in the absorption spectra of the respective first, second or third target gas contained within the respective first, second or third reference cells.

This allows the present invention to be implemented for a number of different target gases. As will be appreciated by a person skilled in the art, the microprocessor 49 can be adapted to select the bias voltage applied to the driver elements so that the spectrometer effectively analyses the concentration of either the first, second or third target gases, depending on which cIPF 45,65,85 has its transmission spectra aligned with the absorption spectra of the respective target gas.

What is claimed is:

1. A spectrometer for determining the concentration of a substance within a sample, the spectrometer comprising:
   a. a radiation source for supplying radiation to the sample to be measured;
   b. a filter for filtering radiation transmitted by the sample, the filter having a number of pass bands at wavelengths corresponding to absorption peaks in the absorption spectrum of the sample to be detected, the filter being responsive also to a separate applied signal to modulate the wavelengths of the pass bands; and,
   c. a detector for detecting the filtered radiation, the detector being responsive to the applied signal to determine the relative intensities of the maxima and minima in the absorption spectra of the substance, characterized in that the radiation source is selectively activated in response to said separate applied signal.

2. A spectrometer according to claim 1 wherein the detector further comprises a processor for processing signals output therefrom.

3. A spectrometer for detecting the concentration of a substance within a sample, the spectrometer comprising:
   a. a reference cell containing a quantity of the substance;
   b. a sample cell for containing the sample in use;
   c. a radiation source for supplying radiation to the reference cell and the sample cell;
   d. first and second filters for filtering radiation transmitted by the reference and sample cells respectively, each filter having a number of pass bands and being responsive to a common applied signal to modulate the wavelengths of the pass bands;
   e. first and second detectors for detecting the filtered radiation from the first and second filters respectively, the detectors being responsive to the applied signal to measure the intensity of the filtered radiation; and,
   f. a processor responsive to the first detector for controlling the common applied signal.

4. A spectrometer according to claim 3, wherein the first and second detectors operate to repeatedly sample the intensity of the filtered radiation at predetermined time intervals.

5. A spectrometer according to claim 4, wherein the processor controls the common applied signal such that the first detector detects radiation corresponding to maxima and minima in the absorption spectra of the substance at adjacent sampling times.

6. Apparatus according to claim 5, wherein the signal includes a bias signal and an alternating signal, and wherein the processor controls the bias signal such that the pass bands of the filter correspond to either the maxima or minima of the spectra of the substance when no alternating signal is applied.

7. A spectrometer according to claim 5, wherein the second detector samples the radiation transmitted by the second filter at the same time the first detector samples the radiation transmitted by the first filter.

8. A spectrometer according to claim 7, wherein the processor is responsive to the second detector to determine the difference in the intensity of the radiation transmitted between adjacent samplings to thereby calculate the relative intensities of the maxima and minima in the absorption spectra of the substance.

9. A spectrometer according to any of claim 3, the spectrometer being adapted to detect the concentration of a number of different substances within the sample, the spectrometer comprising:
   a. a number of reference cells, each reference cell containing a quantity of a respective substance whose concentration in the sample is to be determined;
   b. a number of filters for filtering radiation transmitted by a respective reference cell, each filter having a number of pass bands and being responsive to a common applied signal to modulate the wavelengths of the pass bands; and,
   c. a number of detectors, each detector detecting the filtered radiation from a respective filter, the detectors being responsive to the common applied signal to measure the intensity of the filtered radiation.

10. A spectrometer according to claim 9, wherein to detect the concentration of a given one of the substances the processor controls the common applied signal such that the detector associated with the reference cell containing the substance whose concentration is to be detected, detects radiation corresponding to maxima and minima in the absorption spectra of the substance at adjacent sampling times.

11. A spectrometer according to claim 1, wherein the filter comprises:
   a. a first polarizer for polarizing received radiation;
   b. a birefringent element responsive to the applied signal, wherein the birefringent element modifies the polarization of the polarized radiation in accordance with the wavelength of the radiation and the applied signal; and,
   c. a second polarizer for polarizing the radiation transmitted by the birefringent element.

12. A spectrometer according to claim 11, wherein the birefringent element comprises:
   i. a first birefringent member; and,
   ii. an optically isotropic member, the optically isotropic member being responsive to a force applied thereto to generate a birefringence.

13. A spectrometer according to claim 11, wherein the birefringent element is common to all the filters.

14. A spectrometer according to claim 13, wherein the optically isotropic member is common to all the filters.

15. A spectrometer according to claim 1, wherein the radiation source comprises an LED.

16. A spectrometer according to claim 1, the spectrometer further comprising a collimator positioned between the radiation source and the sample for collimating the radiation emitted by the radiation source.

17. A spectrometer according to claim 3, the spectrometer further comprising a bandpass filter positioned between the cell and the respective filter.

18. A spectrometer according to claim 1, wherein the filter is a CIPF.

19. A spectrometer according to claim 3, wherein the or each filter comprises:
   a. a first polarizer for polarizing received radiation;
   b. a birefringement element responsive to the applied signal, wherein the birefringent element modifies the polarization of the polarized radiation and the applied signal; and,
   c. a second polarizer for polarizing the radiation transmitted by the birefringement element.

20. A spectrometer according to claim 3, wherein the radiation source comprises and LED.

21. A spectrometer according to claim 3, the spectrometer further comprising a collimator positioned between the radiation source and the sample for collimating the radiation emitted by the radiation source.

22. A spectrometer according to claim 3, the spectrometer further comprising a bandpass filter positioned between the or each cell and the or each respective filter.

23. A spectrometer according to claim 3, wherein the filter is a CIPF.

* * * * *